US010444140B1

(12) United States Patent
Hovorka et al.

(10) Patent No.: US 10,444,140 B1
(45) Date of Patent: Oct. 15, 2019

(54) THETA-THETA SAMPLE POSITIONING STAGE WITH APPLICATION TO SAMPLE MAPPING USING REFLECTOMETER, SPECTROPHOTOMETER OR ELLIPSOMETER SYSTEM

(71) Applicants: Griffin A. P. Hovorka, Lincoln, NE (US); Martin M. Liphardt, Lincoln, NE (US); Galen L Pfeiffer, Roca, NE (US)

(72) Inventors: Griffin A. P. Hovorka, Lincoln, NE (US); Martin M. Liphardt, Lincoln, NE (US); Galen L Pfeiffer, Roca, NE (US)

(73) Assignee: J.A. WOOLLAM CO., INC., Lincoln, NE (US)

(*) Notice: Subject to any disclaimer, the term of this patent is extended or adjusted under 35 U.S.C. 154(b) by 0 days.

(21) Appl. No.: 16/501,699

(22) Filed: May 23, 2019

Related U.S. Application Data

(60) Provisional application No. 62/919,525, filed on Mar. 18, 2019.

(51) Int. Cl.
*G01J 3/42* (2006.01)
*G01N 21/01* (2006.01)
*G01N 21/55* (2014.01)
*G01N 21/21* (2006.01)
*G01N 21/31* (2006.01)

(52) U.S. Cl.
CPC .............. *G01N 21/01* (2013.01); *G01J 3/42* (2013.01); *G01N 21/211* (2013.01); *G01N 21/31* (2013.01); *G01N 21/55* (2013.01)

(58) Field of Classification Search
CPC ...... G01N 21/01; G01N 21/31; G01N 21/211; G01N 21/21; G01J 3/42; G01J 21/55; G01J 4/00; G01J 4/04; G01J 3/02; G01J 2/02
See application file for complete search history.

(56) References Cited

U.S. PATENT DOCUMENTS

| | | | |
|---|---|---|---|
| 6,941,231 B2 | 9/2005 | Zeroug et al. | |
| 7,505,134 B1 | 3/2009 | Johs et al. | |
| 7,672,502 B2 | 3/2010 | Osada et al. | |
| 7,746,471 B1 | 6/2010 | Johs et al. | |
| 7,746,472 B1 | 6/2010 | Johs et al. | |
| 7,872,751 B2 | 1/2011 | Liphardt et al. | |
| 8,059,276 B2 | 11/2011 | Hilfiker et al. | |
| 8,248,606 B1 | 8/2012 | Liphardt et al. | |
| 8,248,607 B1 | 8/2012 | Herzinger et al. | |
| 8,339,603 B1 | 12/2012 | Liphardt et al. | |
| 8,436,994 B2 | 5/2013 | Liphardt et al. | |
| 8,570,513 B2 | 10/2013 | Hilfiker et al. | |
| 9,347,768 B1 | 5/2016 | Pfeiffer et al. | |
| 9,933,357 B1 | 4/2018 | He et al. | |
| 2017/0176348 A1* | 6/2017 | Leem | G01N 21/956 |

* cited by examiner

*Primary Examiner* — Abdullahi Nur
(74) *Attorney, Agent, or Firm* — James D. Welch

(57) ABSTRACT

A sample positioning system having two rotation elements with offset therebetween, to the second of which rotation elements is affixed a sample supporting stage. The rotation axes of the two rotation element are parallel, or substantially so. The sample positioning system finds application in the mapping of samples by Metrology systems such as Reflectometer, Spectrophotometer and Ellipsometer systems.

16 Claims, 6 Drawing Sheets

THETA-THETA SAMPLE POSITIONING STAGE WITH APPLICATION TO SAMPLE MAPPING USING REFLECTOMETER, SPECTROPHOTOMETER OR ELLIPSOMETER SYSTEM

TECHNICAL AREA

The present invention relates to sample positioning systems, and more particularly to a sample positioning system that comprises two rotation elements that have an offset therebetween, said two rotation elements having parallel, or substantially so, rotation axes. The second rotation element has a sample supporting stage affixed thereto. Said sample positioning system finds application in the mapping of samples by Reflectometer, Spectrophotometer and Ellipsometer systems.

BACKGROUND

It is known to access multiple locations on a sample. (eg. during mapping procedures), using Reflectometer, Spectrophotometer and Ellipsometer systems. See for instance, U.S. Pat. Nos. 8,436,994, 7,872,751, 8,248,606, and 8,339,603 to Liphardt et al., U.S. Pat. Nos. 7,505,134, 7,746,471 and 7,746,472 to Johs et al., U.S. Pat. Nos. 8,059,276, 8,570,513 to Hilfiker et al., U.S. Pat. No. 9,933,357 to He et al., U.S. Pat. No. 8,248,607 to Herzinger et al. and U.S. Pat. No. 9,347,768 to Pfeiffer et al.

The most direct approach to accomplishing sample mapping applies two translation elements each comprising a fixed part and a translatable part such that linear translation can be affected between said fixed and translatable parts along a given axis within each element. The fixed part of the second translation element is attached to the translatable part of the first element, with the translation axis of the second element not parallel to that of the first. Ideally, the translation axes of the two elements are roughly perpendicular. A stage for supporting a sample is affixed to said translatable part of said second translation element. In use, the translatable parts of each translation element are caused to linearly translate along their respective axes, allowing a beam to access substantially any location on a sample placed on said stage. Such a mapping system is commonly referred to as an X-Y translation system. Another approach involves a translation element comprising a fixed part and a translatable part and a rotation element comprising a fixed part and a rotatable part, such that in use rotation between said fixed part and said rotatable part can be affected. The fixed part of the rotation element is attached to the translatable part of the first element, with the translation axis of the first element oriented perpendicular to the rotation axis of the second element. A stage for supporting a sample is affixed to said rotatable part of said rotation element. In use the translatable part of the translation element is caused to linearly translate with respect to the fixed element, and the rotatable part of the rotation element is caused to rotate with respect to the fixed element, allowing a beam to access substantially any location on a sample placed on said stage. Such a mapping system is commonly referred to as an R-Theta translation system.

In order to map a circular sample with radius R using the first approach, each translation element must have a linear range of at least 2R and the footprint of the sample translation is approximately 4R by 4R.

With the second approach, the rotation element can rotate to substantially any angle, and the necessary range of translation is reduced to 1R. The footprint of sample translation is approximately 3R×2R, resulting in a more compact system.

Another approach provides that a first rotatable element is secured at a first fixed part, and a second rotatable element is secured at a second fixed element, which can be visualized as a like an old record player.

Summarizing, Metrology systems used in sample mapping can comprise a first element allows motion in, say an "X" direction, and the second in a "Y" direction. The second element is slidably affixed to the first element, and has a sample supporting stage slidably affixed thereto. In use specific "X"-"Y" positions on a sample which is placed on the stage can be accessed by an electromagnetic beam by slidably moving the second element with respect to the first, and by slidably moving the stage with respect to the first element. Another approach involves a first element to which is slidably affixed a second element, which second element has a stage for supporting a sample rotatably affixed thereto. In use the second element is slid to a location with respect to the first element, and then the stage is rotated to provide access to specific locations on a sample placed on the stage. The first approach requires a system which is as wide as it is deep to allow both "X" and "Y" motions. The second approach can be implemented by a system than needs only about half the width, (ie. the required travel range of the stage is only the radius of the sample stage). Another approach, which again provides a compact system, can be envisioned as being similar to an old record player. A first element is rotatably affixed to a support, as is a second element to which is attached a stage for supporting a sample. The second element is rotatably affixed at distance from the point at which the first element is rotatably affixed. In use the first element is rotated about the position at which it is rotatably affixed to the support so that a distal end thereof is positioned adjacent to a sample which is placed on said stage, and said stage is rotated about the position at which it is rotatably attached. Again, specific locations on a sample can be accessed by an electromagnetic beam.

Even in view of the foregoing, need remains for improved compact systems which allow accessing specific locations on a sample, and thereby allow mapping samples by Reflectometer, Spectrophotometer and Ellipsometer systems.

DISCLOSURE OF THE INVENTION

The present invention theta-theta mapping system involves the use of two rotation elements that have their rotation axes laterally displaced from one another as a parallel offset. A stage for supporting a sample is affixed to the second rotation element and rotating both rotation stages allows a sample to be mapped.

The theta-theta approach, provides that the footprint of sample translation is approximately that of the second approach (identified in the Background Section), however several benefits are realized. Rotation elements are convenient for mapping systems because wires and hoses can be passed directly through the axis of rotation of the element and complicated translating cable tracks are unnecessary. In addition, rotation elements are easier to manufacture to tight tolerances than translation elements because generally it is easier to make a perfectly round part than to make a perfectly flat part over a relatively much larger surface. The maximum measurable radius of an X-Y system is half the translation range of the smallest translation element. The measurable radius of an R-Theta system is equal to the translation range of the translation element. Because translation elements are usually substantially longer than their range, these restrictions limit the minimum size of a mapping system. The measurable radius of a theta-theta system is equal to twice the distance between the axes of the two rotation elements, meaning the mapping system of a theta-theta system can be much more compact, even though the translation footprint will be similar. Furthermore, a theta-theta mapping system allows the sample stage to be translated past its normal range to access each point thereof without increasing the size of the mapping system. This is not possible with an X-Y translation system or R-Theta translation system without increasing its size. Moving a sample stage out of the normal range might have benefits when loading a sample onto the stage or when performing maintenance.

The present invention can be described as a system for positioning a sample relative to a sample investigating beam of electromagnetic radiation via two rotations, said system comprising:

a) a support;

b) a first rotation element comprising a first fixed part and a first rotatable part having a first rotation axis, such that in use rotation motion between said first fixed part and said first rotatable part can be affected, said first fixed part being attached to said support;

c) a second rotation element comprising a second fixed part and a second rotatable part having a second rotation axis, such that in use rotation motion between said second fixed part and said second rotatable part can be affected, said second fixed part being attached to said first rotatable part of said first rotating element such that said second rotation axis is laterally displaced from said first rotation axis;

said rotation axes of both said first and second rotation element being parallel, or substantially so;

d) a stage for supporting a sample affixed to said second rotatable part of said second rotation element.

In use a sample is placed on said stage for supporting a sample and said first rotatable part of said first rotation element is caused to rotate about said first rotation axis, and said second rotatable part of said second rotation element is caused to rotate about said second rotation axis, thereby enabling said sample investigation beam of electromagnetic radiation to access substantially any location on said sample.

A present inventions method of investigating a sample then comprises the steps of:

a) providing a metrology system for investigating locations on a sample with a beam of electromagnetic radiation comprising a source of electromagnetic radiation and a detector of electromagnetic radiation oriented so that a beam of electromagnetic radiation provided by said source of electromagnetic radiation is directed to interact with an intended location on said sample and reflect therefrom into said detector of electromagnetic radiation;

said system being distinguished by further comprising a system for positioning said sample relative to said beam of electromagnetic radiation via two rotations, said system for positioning a sample comprising:

a') a support;

b') a first rotation element comprising a first fixed part and a first rotatable part having a first rotation axis, such that in use rotation motion between said first fixed part and said first rotatable part can be affected, said first fixed part being attached to said support;

c') a second rotation element comprising a second fixed part and a second rotatable part having a second rotation axis, such that in use rotation motion between said second fixed part and said second rotatable part can be affected, said second fixed part being attached to said first rotatable part of said first rotating element such that said second rotation axis is laterally displaced from said first rotation axis;

said rotation axes of both said first and second rotation element being parallel, or substantially so;

d') a stage for supporting a sample affixed to said second rotatable part of said second rotation element;

such that in use a sample is placed on said stage for supporting a sample and said first rotatable part of said first rotation element is caused to rotate about said first rotation axis, and said second rotatable part of said second rotation element is caused to rotate about said second rotation axis, thereby enabling said sample investigation beam of electromagnetic radiation to access substantially any location on said sample b) placing a sample having a surface on said stage for supporting a sample;

practicing steps c) and d) in either order, said steps c) and d) being:

c) causing said source of electromagnetic radiation to direct a beam of electromagnetic radiation at said sample at an angle of incidence to the surface thereof;

d) causing at least one of:

said first element rotatably affixed to said support; and said second element rotatably affixed to a location on said first element distal from the point of its rotatable affixation to said support;

to rotate so that said beam of electromagnetic radiation impinges on said sample at a desired location, and said detector of electromagnetic radiation outputs a signal; and e) accepting and analyzing the data provided by said detector of electromagnetic radiation.

Said method can further comprise:

f) before step e) causing both said source and detector of electromagnetic radiation to move toward or away from the sample, and/or causing the source and detector of electromagnetic radiation to rotate about a point at which the beam of electromagnetic radiation interacts with said sample.

This step is useful where a sample surface is not absolutely uniform, and different points thereon present with somewhat different distances between said sample surface, and the source and detector, and/or where sample surface differences at different points thereon cause a different angle of in incidence of the electromagnetic beam be present.

Said method can also further comprise:

repeating steps c), d) and e) a desired plurality of times to provide a mapping of said sample.

Said method can also further comprise:

repeating steps c), d), e) and f) a desired plurality of times to provide a mapping of said sample.

Said method can further comprise monitoring the surface of the sample with an oblique angle of incidence imaging system during practice thereof.

Said method can also involve setting the angle of incidence at which the beam of electromagnetic radiation approaches the sample surface in step c).

In view of the foregoing, it is disclosed that the present invention can be described as a system for positioning a sample relative to a sample investigating beam of electromagnetic radiation via two rotations, said system comprising:

a) a support;

b) an first element rotatably affixed to said support about a first rotation axis;

c) a second element rotatably affixed to a location on said first element distal from the point of its rotatable affixation to said support, said second element being rotatable about a second rotation axis, said second element comprising a stage for supporting a sample.

The rotation axes of both the first and second elements are parallel, or substantially so.

In use a sample is placed on said stage for supporting a sample and said first element is caused to rotate about its point of rotatable affixation to said support, and said second element is caused to rotate about its point of rotatable affixation to said first element, thereby enabling said electromagnetic beam to access substantially any location on said sample.

The electromagnetic beam can be provided by a reflectometer or spectrophotometer system comprising a source of electromagnetic radiation and a detector of electromagnetic radiation oriented so that a beam of electromagnetic radiation provided by said source of electromagnetic radiation is directed to interact with an intended location on said sample and reflect therefrom into said detector of electromagnetic radiation.

The electromagnetic beam can alternatively be provided by an ellipsometer system comprising a source of electromagnetic radiation, a polarizer, an analyzer, and a detector of electromagnetic radiation oriented so that said beam of electromagnetic radiation radiation provided by said source of electromagnetic radiation is directed to pass through said polarizer, interact with an intended location on said sample and reflect therefrom, then pass through said analyzer and into said detector of electromagnetic radiation.

Said ellipsometer system can also further comprise at least one compensator between at least one selection from the group consisting of:

between said source of electromagnetic radiation and said stage for supporting a sample; and between said stage for supporting a sample and said detector of electromagnetic radiation.

The present invention is also a metrology system for investigating locations on a sample with a beam of electromagnetic radiation comprising a source of electromagnetic radiation and a detector of electromagnetic radiation oriented so that a beam of electromagnetic radiation provided by said source of electromagnetic radiation is directed to interact with an intended location on said sample and reflect therefrom into said detector of electromagnetic radiation.

Said system is distinguished by further comprising a system for positioning said sample relative to said beam of electromagnetic radiation via two rotations, said system for positioning a sample comprising:
  a) a support;
  b) an first element rotatably affixed to said support about a first rotation axis;
  c) a second element rotatably affixed to a location on said first element distal from the point of its rotatable affixation to said support, said second element being rotatable about a second rotation axis, said second element comprising a stage for supporting a sample, wherein the rotation axes of both the first and second elements are parallel, or substantially so.

In use a sample is placed on said stage for supporting a sample and said first element is caused to rotate about its point of rotatable affixation to said support, and said second element is caused to rotate about its point of rotatable affixation to said first element, thereby enabling said electromagnetic beam to access substantially any location on said sample.

The metrology system can be a reflectometer or spectrophotometer system comprising said source of electromagnetic radiation and said detector of electromagnetic radiation.

The metrology system electromagnetic beam can be provided by an ellipsometer system comprising said source of electromagnetic radiation, a polarizer, an analyzer, and said detector of electromagnetic radiation oriented so that said beam of electromagnetic radiation radiation provided by said source of electromagnetic radiation is directed to pass through said polarizer, interact with said intended location on said sample and reflect therefrom, then pass through said analyzer and into said detector of electromagnetic radiation. Said ellipsometer system can further comprise at least one compensator between at least one selection from the group consisting of:

between said source of electromagnetic radiation and said stage for supporting a sample; and between said stage for supporting a sample and said detector of electromagnetic radiation.

The present invention is also a method of investigating a sample, comprising the steps of:
  a) providing a metrology system comprising:
  a') a support;
  b') an first element rotatably affixed to said support about a first rotation axes;
  c') a second element rotatably affixed to a location on said first element distal from the point of its rotatable affixation to said support, said second element being rotatable about a second rotation axes, said second element comprising a stage for supporting a sample, wherein the rotation axes of both the first and second elements are parallel, or substantially so;
  b) placing a sample having a surface on said stage for supporting a sample;
practicing steps c) and d) in either order, said steps c) and d) being:
  c) causing said source of electromagnetic radiation to direct a beam of electromagnetic radiation at said sample at an angle of incidence to the surface thereof;
  d) causing at least one of:
    said first element rotatably affixed to said support; and
    said second element rotatably affixed to a location on said first element distal from the point of its rotatable affixation to said support;
  to rotate so that said beam of electromagnetic radiation impinges on said sample at a desired location, and said detector of electromagnetic radiation outputs a signal; and
  e) accepting and analyzing the data provided by said detector of electromagnetic radiation.

Said method can further comprise:
  f) before step e) causing both said source and detector of electromagnetic radiation to move toward or away from the sample, and/or causing the source and detector of electromagnetic radiation to rotate about a point at which the beam of electromagnetic radiation interacts with said sample.

This step is useful where a sample surface is not absolutely uniform, and different points thereon present with somewhat different distances between said sample surface, and the source and detector, and/or where sample surface differences at different points thereon cause a different angle of in incidence of the electromagnetic beam be present.

Said method can also further comprise:
  repeating steps c), d) and e) a desired plurality of times to provide a mapping of said sample.

Said method can also further comprise:
repeating steps c), d), e) and f) a desired plurality of times to provide a mapping of said sample.

Said method can also involve setting the angle of incidence at which the beam of electromagnetic radiation approaches the sample surface in step c).

The present invention will be better understood by reference to the Detailed Description Section of this Disclosure, in conjunction with the Drawings.

DETAILED DESCRIPTION

Figure 1:
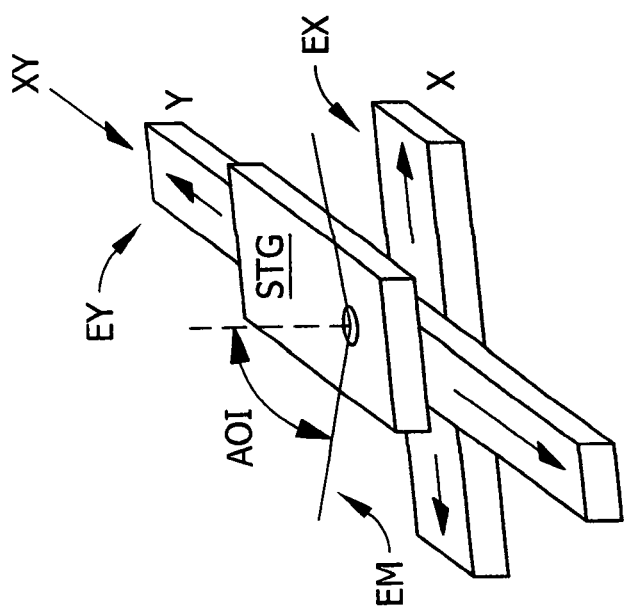
FIG. 1 shows a prior art X-Y system for adjusting the position of a sample on a stage.

Turning now to the Drawings, FIG. 1 shows a known (XY) approach to accomplishing sample mapping via adjusting the position of a sample on a stage, which involves applying two elements (Ex) and (Ey) which are at right angles to one another. The first element (Ex) allows motion in an "X" direction, and the second in a "Y" direction. The second element (Ey) is slidably affixed to the first element (Ex), and has a sample supporting stage (STG) slidably affixed thereto. In use specific "X"-"Y" positions on a sample which is placed on the stage (STG) can be accessed by an electromagnetic beam (Em) by slidably moving the second element (Ey) with respect to the first (Ex), and by slidably moving the stage (STG) with respect to the first element (Ex).

Figure 2:
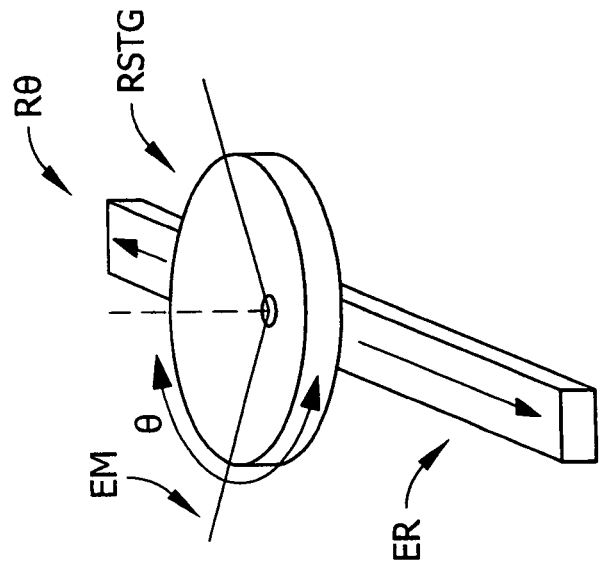
FIG. 2 shows a prior art R-e system for adjusting the position of a sample on a stage.

FIG. 2 shows another approach (R-Θ) which involves a radial element (Er) to which is slidably affixed a second element (RSTG), which second element is a stage for supporting a sample rotatably affixed thereto. In use the second element (RSTG) is slid to a location with respect to the first element (Er), and then the stage (STG) is rotated to provide access to specific locations on a sample placed thereon.

It is noted that the first approach requires a system which is as wide as it is deep to allow both "X" and "Y" motions. The second approach can be implemented by a system than need by only about half as deep as wide, (ie. the required travel range of the stage is only the radius thereof).

Figure 3:
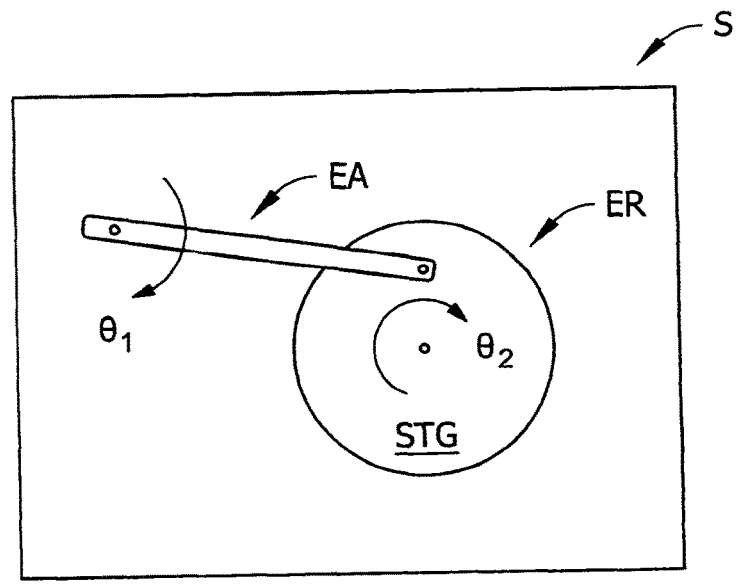
FIG. 3 shows a present invention $\Theta_1$-$\Theta_2$ system for adjusting the position of a sample on a stage.

Another approach is shown in FIG. 3, which again provides a compact system. It can be envisioned as being similar to an old record player. A first element (EA) is rotatably affixed to a support (S), as is a second element (ER) to which is attached a stage (STG) for supporting a sample. The second element (ER) is rotatably affixed to the support (S) at distance from the point at which the first (EA) element is rotatably affixed. In use the first element (EA) is rotated about the position at which it is rotatably affixed to the support (S) so that a distal position thereof is positioned adjacent to a sample which is placed on said stage (STG), and said stage (STG) is rotated about the position at which it is rotatably attached to said support (S). Again, specific locations on a sample can be accessed by an electromagnetic beam much as demonstrated in FIGS. 1 and 2. Also, it should be noted that the ($\Theta_1$-$\Theta_2$) is as compact as is the (R-$\Theta_2$) system, both requiring a sample travel range of the stage which is on the order of the radius of the sample stage.

Figure 4A:
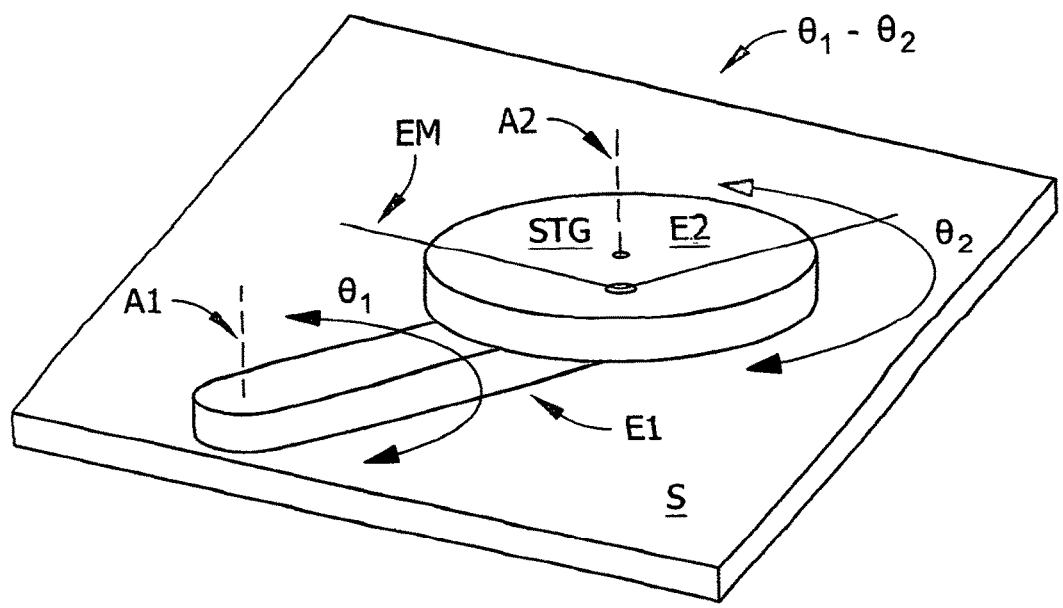
FIG. 4A shows a system which, while known, is not believed to have been applied to adjusting the position of a sample on a stage.

FIG. 4A is the preferred embodiment of the present invention metrology system, which is well suited for sample mapping. Shown is a system for positioning a sample relative to a sample investigating beam (EM) of electromagnetic radiation via two rotations, said system comprising:

a) a support (S);
b) a first element (E1) rotatably affixed to said support (S) about a first rotation axis (A1);
c) a second element (E2) rotatably affixed to a location on said first element (E1) distal from the point of its rotatable affixation to said support, said second element (E2) being rotatable about a second rotation axis (A2), and said second element (E2) comprising a stage (STG) for supporting a sample.

Note that the rotation axes of both the first (A1) and second (A2) elements are parallel, or substantially so. In use a sample (SA)(see FIGS. 5-7) is placed on said stage (STG) for supporting a sample and said first element (E1) is caused to rotate about its point of rotatable affixation to said support (S), and said second element (E2) is caused to rotate about its point of rotatable affixation to said first element (E1), thereby enabling said electromagnetic beam (EM) to access substantially any location (M) on said sample placed on said stage (STG), as identified determined via Eqns. 1 and 2. The FIGS. 4A-4D embodiment is again much more compact that the embodiment of FIG. 1, and is on the same order compactness as the embodiment of FIG. 2. This, the required travel range of the stage is only the radius thereof.

It is noted that:
Element (S) can be referred to as a first fixed element;
Element (E1) can be referred to as a first rotation element;
an Element coincident with Axis (A2) which projects from Element (E1) (not directly shown), and is rotatably affixed to Element (E2), can be referred to as a second fixed element; and
Element (E2) can be referred to as a second rotation element.

Figure 4B:
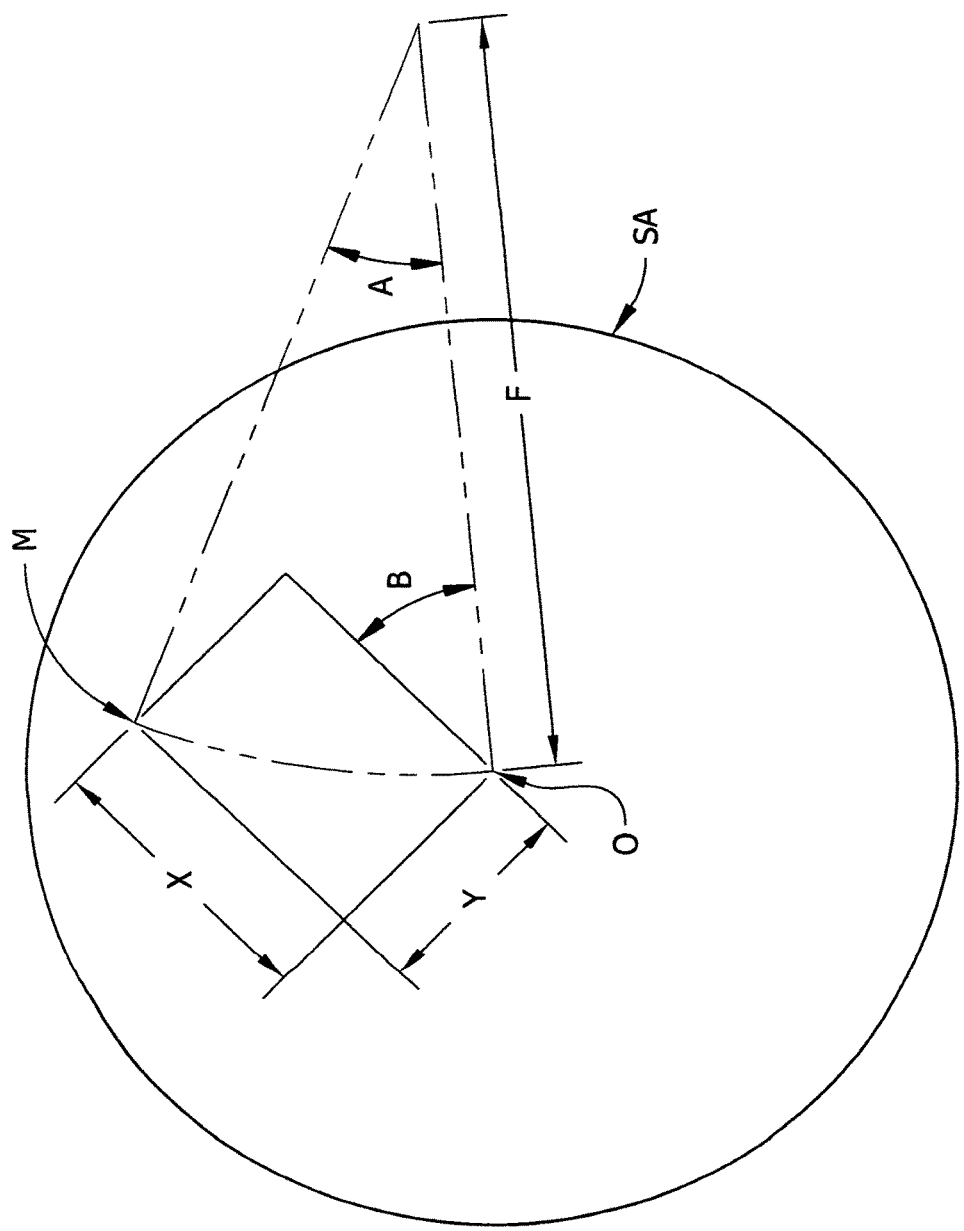
FIG. 4B shows relationships between angles of rotation of elements (E1) and (E2) in FIG. 4A, and the (X)-(Y) coordinates of a point (M) with respect to the origin (O) of a sample FIGS. 4C and 4D demonstrate how a rotation angle (A) affects the location of point (M) on a sample (SA).

FIG. 4B shows a representative sample (SA) and relationships between rotation angles (A) and (B), and the (X) and (Y) parameters of an accessed point (M). Note, (f) is the distance between (A1) and (A2) in FIG. 4. The Equations governing how point (M) relates to the origin (O) are:

$$A = 2\, \text{Arc sin}((X^2+Y^2)^{1/2}/2F);\ \text{and} \qquad \text{Eq. 1}$$

$$B = \text{Arc tan}(Y/X) + A/2. \qquad \text{Eq. 2}$$

Figure 4C:
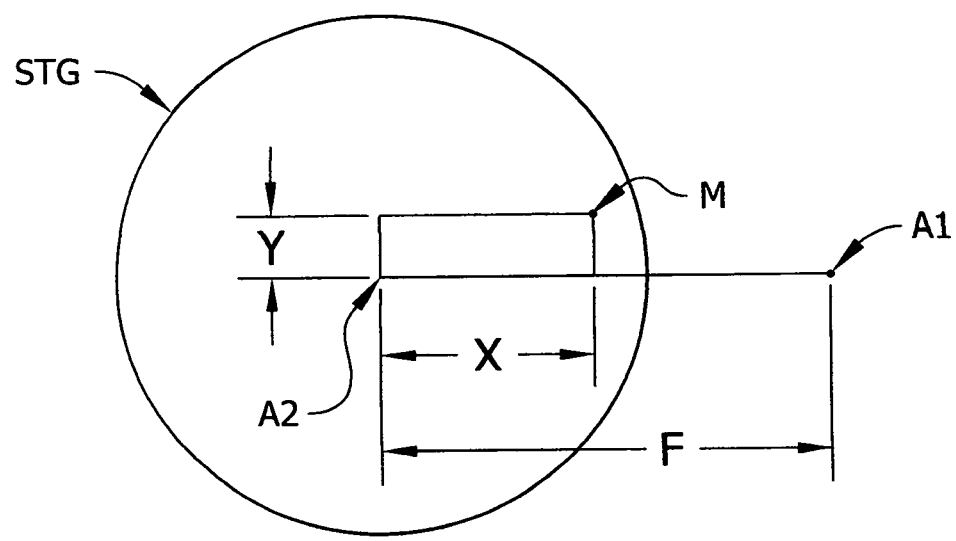
Figure 4D:
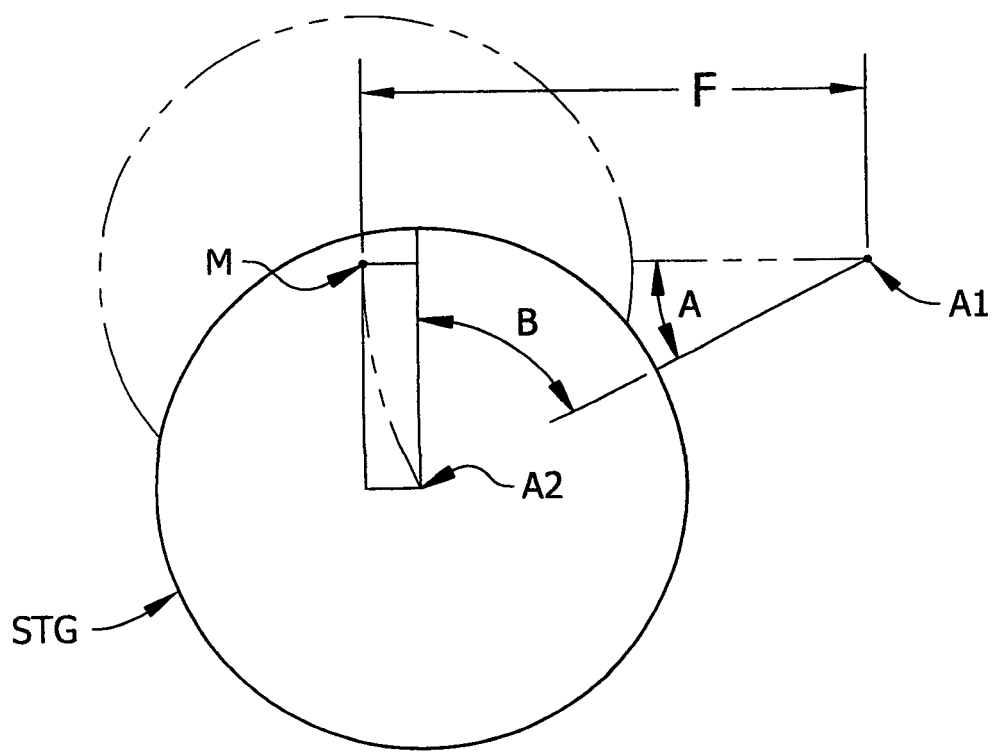

FIGS. 4C and 4D are included to show how a rotation angle (A) in FIG. 4A affects the position of point (M) on a sample.

Figure 5:
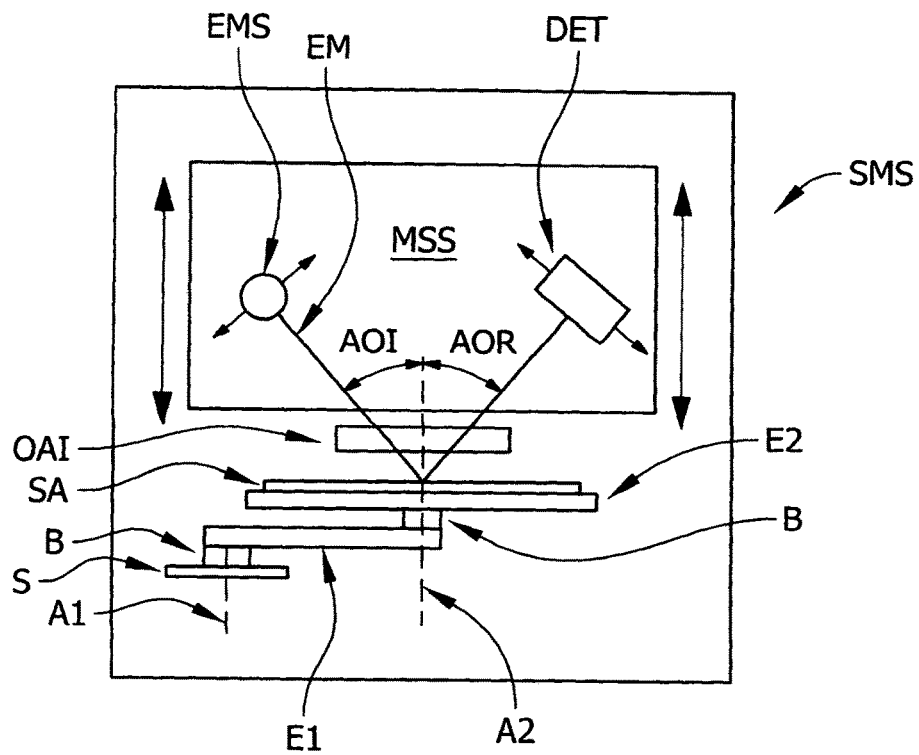
FIG. 5 shows a front view of a present invention sample mapping system.

FIG. 5 shows a front view of a present invention sample (SA) mapping system (SMS). For orientation, note the locations of elements (E1) and (E2) and their rotation axes (A1) and (A2) from FIG. 4. Bearings (B) are shown to demonstrate functional interconnections between element (E1) and the support(S), and element (E2). Any rotation supporting equivalent can be substituted. Also shown is a metrology system situated above the system of elements (E1) and (E2), which comprises a source of electromagnetic radiation (EMS) and a detector (DET) thereof. Note that said source of electromagnetic radiation (EMS) and detector (DET) thereof are affixed to a metrology system securing plate (MSS) which enables simultaneously moving both source of electromagnetic radiation (EMS) and detector (DET) upward or downward to achieve good positioniong of the beam of electromagnetic radiation (EM) onto an intended spot on sample (SA), which is placed on the upward facing surface of element (E2), said upper surface serving as a stage for supporting a sample (SA). Also shown is an oblique angle sample surface imaging system (OAI). As discussed below this system enables viewing the surface of the sample (SA) without focusing and distortion problems. It is conveniently located out of the way of other components, and achieves its purpose by applying a system which meets the Schiempfug Condition, in combination with a telecentric lens which overcomes Keystone (ie. image distortion) error. In use a user can use the (OAI) to view the location on the sample (SA) the beam of electromagnetic radiation is investigating. Further, note the indication of the angle-of-incidence (AOI) and angle-of-reflection (AOR), which it is to be understood can also be adjusted as indicated by the positive and negative slope direction arrows, respectively, on the source of electromagnetic radiation, and detector thereof.

Figure 6:
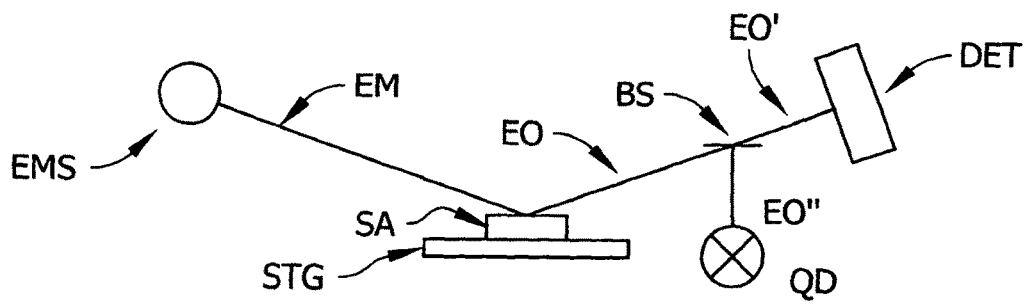
FIG. 6 demonstrates a system for monitoring the height that the a source of electromagnetic radiation and a detector thereof are located above the surface of a sample.

FIG. 6 demonstrates a system for monitoring changes in the height that a source (EMS) of a beam of electromagnetic radiation (EM) and a detector (DET) thereof are located above the surface of a sample (SA), as well as determining changes in the tip/tilt (ie. angle-of incidence and plane of incidence) of a sample in a sample mapping system (SMS). Typically, a user will determine an optimum height by experimentally changing the distance between the combined source (EMS) and detector (DET) and the sample (SA) surface by simply changing it and noting where the detector (DET) provides a maximum (or some other desired) value when (EO') enters thereinto. Note also the beam splitter (BS) and quad detector (QD) that the reflected beam portion (EO") encounters. The output of the quad detector (QD) will change based on changes in the electromagnetic beam angle and plane of incidence. The present invention applies monitored changes in the intensity of beam portion (EO') to control the position of the metrology system securing plate (MSS), and uses detected changes in the output of the quad detector (QD) segments to control adjustments in stage (STG) tip or tilt.

Figure 7A:
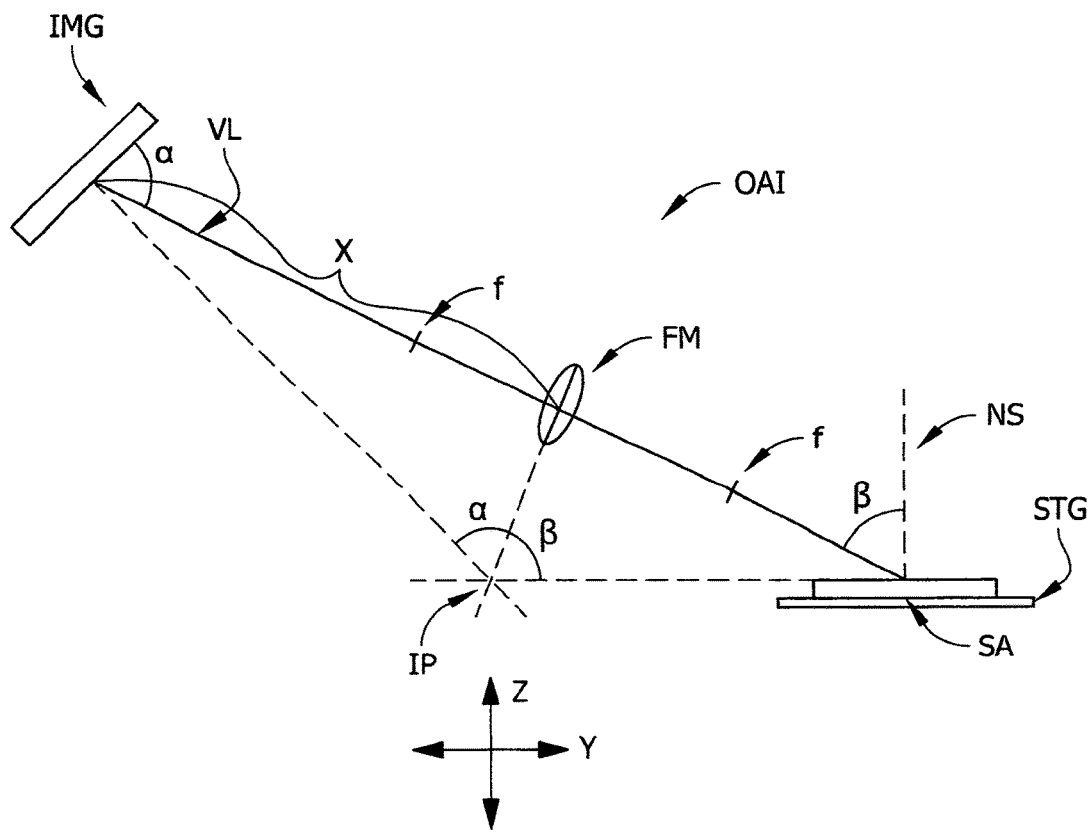
FIG. 7A demonstrates a system meeting the Scheimpflug Condition and which overcomes distortion (ie. Keystone error) in the oblique angle imaging system.

FIG. 7A demonstrates a system meeting the Scheimpflug Condition, and which overcomes distortion (ie. Keystone error) in the oblique angle imaging system (OAI). Note that a camera imaging plate (IMG) is positioned with respect to a sample (SAM) with their surfaces at set angles with respect to one another. Also note the presence of a focusing means (FM) and the various angles identified. The camera's (IMG) viewpoint locus (VL) of a sample (SAM) sample passes through said focusing means (FM) and as a result angles ($\alpha$) and ($\beta$) are defined. When the Equation:

$$\mathrm{Tan}(\alpha) = (X-f)/f\, \mathrm{Tan}(\beta)$$

is satisfied the surface of the sample (SAM) will be in focus over its entire area even though the distances from the camera imaging plate (IMG) vary. The identifier "f" indicates the focal length of the focusing means (FM), and "X" is the distance from the imaging plate (IMG) to the center of the focusing means (FM). The angle ($\alpha$) is the angle between the plane of the imaging plate (IMG) and viewpoint locus, and ($\beta$) is the angle of incidence that the viewpoint locus (VL) makes with respect to a normal to the surface of the sample (SAM). Again, when the various elements are oriented as shown the imaging plate (IMG) plate will have an in-focus view of the entire surface of the surface of the sample (SAM).

Figure 7B:
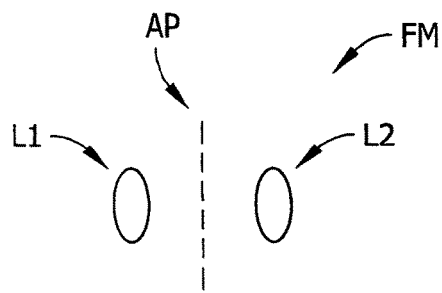
FIG. 7B shows a representative telecentric lens, which in use is positioned as (FM) in FIG. 7A.

FIG. 7B shows a representative telecentric lens, which is positioned as (FM) in FIG. 7A. When a system sequentially consisting of a focusing lens (L1), an aperture (AP) and another focusing lens (L2) is present at the location of the focusing means (FM) in FIG. 7A, the image at the imaging plate (IMG) will also be distortion free (ie. there is no Keystone error present) as well as in focus over the surface of the sample (SAM). It is noted that the criteria that defines a telecentric lens is that at least one of the entry and exit pupils is at infinity or substantially so, where "pupil" refers to either the image or object of the aperture (AP).

It is noted that the terminology "affixation" as used in this document is to be understood to refer a relationship between elements, wherein one element rotates with respect to another element to which it is "rotatably affixed".

Having hereby disclosed the subject matter of the present invention, it should be obvious that many modifications, substitutions, and variations of the present invention are possible in view of the teachings. It is therefore to be understood that the invention may be practiced other than as specifically described, and should be limited in breadth and scope only by the Claims.

We claim:

1. A system for positioning a sample relative to a sample investigating beam of electromagnetic radiation via two rotations, said system comprising:
   a) a support;
   b) a first element rotatably affixed to said support about a first rotation axis;
   c) a second element rotatably affixed to a location on said first element distal from the point of its rotatable affixation to said support, said second element being rotatable about a second rotation axis, said second element comprising a stage for supporting a sample;
   the rotation axes of both the first and second elements being parallel, or substantially so;
   such that in use a sample is placed on said stage for supporting a sample and said first element is caused to rotate about its point of rotatable affixation to said support, and said second element is caused to rotate about its point of rotatable affixation to said first element, thereby enabling said electromagnetic beam to access substantially any location on said sample.

2. A system as in claim 1, wherein the electromagnetic beam is provided by a reflectometer or spectrophotometer system comprising a source of electromagnetic radiation and a detector of electromagnetic radiation oriented so that a beam of electromagnetic radiation provided by said source of electromagnetic radiation is directed to interact with an intended location on said sample and reflect therefrom into said detector of electromagnetic radiation.

3. A system as in claim 1, wherein the electromagnetic beam is provided by an ellipsometer system comprising a source of electromagnetic radiation, a polarizer, an analyzer, and a detector of electromagnetic radiation oriented so that said beam of electromagnetic radiation radiation provided by said source of electromagnetic radiation is directed to pass through said polarizer, interact with an intended location on said sample and reflect therefrom, then pass through said analyzer and into said detector of electromagnetic radiation.

4. A system as in claim 3, in which said ellipsometer system further comprises at least one compensator between at least one selection from the group consisting of:
between said source of electromagnetic radiation and said stage for supporting a sample; and
between said stage for supporting a sample and said detector of electromagnetic radiation.

5. A metrology system for investigating locations on a sample with a beam of electromagnetic radiation comprising a source of electromagnetic radiation and a detector of electromagnetic radiation oriented so that a beam of electromagnetic radiation provided by said source of electromagnetic radiation is directed to interact with an intended location on said sample and reflect therefrom into said detector of electromagnetic radiation;
said system being distinguished by further comprising a system for positioning said sample relative to said beam of electromagnetic radiation via two rotations, said system for positioning a sample comprising:
a) a support;
b) a first element rotatably affixed to said support about a first rotation axis;
c) a second element rotatably affixed to a location on said first element distal from the point of its rotatable affixation to said support, said second element being rotatable about a second rotation axis, said second element comprising a stage for supporting a sample;
the rotation axes of both the first and second elements being parallel, or substantially so;
such that in use a sample is placed on said stage for supporting a sample and said first element is caused to rotate about its point of rotatable affixation to said support, and said second element is caused to rotate about its point of rotatable affixation to said first element, thereby enabling said electromagnetic beam to access substantially any location on said sample.

6. A metrology system as in claim 5, wherein the metrology system is reflectometer or spectrophotometer system comprising said source of electromagnetic radiation and said detector of electromagnetic radiation.

7. A metrology system as in claim 5, wherein the metrology system electromagnetic beam is provided by an ellipsometer system comprising said source of electromagnetic radiation, a polarizer, an analyzer, and said detector of electromagnetic radiation oriented so that said beam of electromagnetic radiation provided by said source of electromagnetic radiation is directed to pass through said polarizer, interact with said intended location on said sample and reflect therefrom, then pass through said analyzer and into said detector of electromagnetic radiation.

8. A system as in claim 7, wherein said ellipsometer system further comprises at least one compensator between at least one selection from the group consisting of:
between said source of electromagnetic radiation and said stage for supporting a sample; and
between said stage for supporting a sample and said detector of electromagnetic radiation.

9. A method of investigating a sample, comprising the steps of:
a) providing a metrology system for investigating locations on a sample with a beam of electromagnetic radiation comprising a source of electromagnetic radiation and a detector of electromagnetic radiation oriented so that a beam of electromagnetic radiation provided by said source of electromagnetic radiation is directed to interact with an intended location on said sample and reflect therefrom into said detector of electromagnetic radiation;
said system being distinguished by further comprising a system for positioning said sample relative to said beam of electromagnetic radiation via two rotations, said system for positioning a sample comprising:
a') a support;
b') an first element rotatably affixed to said support about a first rotation axis;
c') a second element rotatably affixed to a location on said first element distal from the point of its rotatable affixation to said support, said second element being rotatable about a second rotation axes, said second element comprising a stage for supporting a sample;
the rotation axes of both the first and second elements being parallel, or substantially so;
such that in use a sample is placed on said stage for supporting a sample and said first element is caused to rotate about its point of rotatable affixation to said support, and said second element is caused to rotate about its point of rotatable affixation to said first element, thereby enabling said electromagnetic beam to access substantially any location on said sample;
b) placing a sample having a surface on said stage for supporting a sample;
practicing steps c) and d) in either order, said steps c) and d) being:
c) causing said source of electromagnetic radiation to direct a beam of electromagnetic radiation at said sample surface at an angle of incidence thereto;
d) causing at least one of:
said first element rotatably affixed to said support; and
said second element rotatably affixed to a location on said first element distal from the point of its rotatable affixation to said support;
to rotate so that said beam of electromagnetic radiation impinges on said sample at a desired location, and said detector of electromagnetic radiation outputs a signal; and
e) accepting and analyzing the data provided by said detector of electromagnetic radiation.

10. A method as in claim 9, which further comprises:
f) before step e) causing both said source and detector of electromagnetic radiation to move toward or away from the sample, and/or causing the source and detector of electromagnetic radiation to rotate about a point at which the beam of electromagnetic radiation interacts with said sample.

11. A method as in claim 9, which further comprises:
repeating steps c), d) and e) a desired plurality of times to provide a mapping of said sample.

12. A method as in claim 11, which further comprises:
repeating steps c), d), e) and f) a desired plurality of times to provide a mapping of said sample.

13. A method as in claim 9, which further comprises setting the angle of incidence in step c).

14. A method as in claim 9, which further comprises monitoring the surface of the sample with an oblique angle of incidence imaging system during practice thereof.

15. A system for positioning a sample relative to a sample investigating beam of electromagnetic radiation via two rotations, said system comprising:
   a) a support;
   b) a first rotation element comprising a first fixed part and a first rotatable part having a first rotation axis, such that in use rotation motion between said first fixed part and said first rotatable part can be affected, said first fixed part being attached to said support;
   c) a second rotation element comprising a second fixed part and a second rotatable part having a second rotation axis, such that in use rotation motion between said second fixed part and said second rotatable part can be affected, said second fixed part being attached to said first rotatable part of said first rotating element such that said second rotation axis is laterally displaced from said first rotation axis;
said rotation axes of both said first and second rotation element being parallel, or substantially so;
   d) a stage for supporting a sample affixed to said second rotatable part of said second rotation element;
such that in use a sample is placed on said stage for supporting a sample and said first rotatable part of said first rotation element is caused to rotate about said first rotation axis, and said second rotatable part of said second rotation element is caused to rotate about said second rotation axis, thereby enabling said sample investigation beam of electromagnetic radiation to access substantially any location on said sample.

16. A method of investigating a sample, comprising the steps of:
   a) providing a metrology system for investigating locations on a sample with a beam of electromagnetic radiation comprising a source of electromagnetic radiation and a detector of electromagnetic radiation oriented so that a beam of electromagnetic radiation provided by said source of electromagnetic radiation is directed to interact with an intended location on said sample and reflect therefrom into said detector of electromagnetic radiation;
said system being distinguished by further comprising a system for positioning said sample relative to said beam of electromagnetic radiation via two rotations, said system for positioning a sample comprising:
   a') a support;
   b') an first element rotatably affixed to said support about a first rotation axis;
   c') a second element rotatably affixed to a location on said first element distal from the point of its rotatable affixation to said support, said second element being rotatable about a second rotation axis, said second element comprising a stage for supporting a sample;
the rotation axes of both the first and second elements being parallel, or substantially so;
such that in use a sample is placed on said stage for supporting a sample and said first element is caused to rotate about its point of rotatable affixation to said support, and said second element is caused to rotate about its point of rotatable affixation to said first element, thereby enabling said electromagnetic beam to access substantially any location on said sample;
   b) placing a sample having a surface on said stage for supporting a sample;
practicing steps c) and d) in either order, said steps c) and d) being:
   c) causing said source of electromagnetic radiation to direct a beam of electromagnetic radiation at said sample at an angle of incidence to the surface thereof;
   d) causing at least one of:
   said first element rotatably affixed to said support; and
   said second element rotatably affixed to a location on said first element distal from the point of its rotatable affixation to said support;
to rotate so that said beam of electromagnetic radiation impinges on said sample at a desired location, and said detector of electromagnetic radiation outputs a signal; and
   e) accepting and analyzing the data provided by said detector of electromagnetic radiation.

* * * * *